(12) United States Patent
Carpenter

(10) Patent No.: US 9,968,474 B2
(45) Date of Patent: May 15, 2018

(54) CORRECTIVE CERVICAL STRETCHING DEVICE

(71) Applicant: Gebo LLC, Pleasantville, NY (US)

(72) Inventor: Thomas A. Carpenter, Yorktown Heights, NY (US)

(73) Assignee: GEBO LLC, Pleasantville, NY (US)

( * ) Notice: Subject to any disclaimer, the term of this patent is extended or adjusted under 35 U.S.C. 154(b) by 85 days.

(21) Appl. No.: 14/570,120

(22) Filed: Dec. 15, 2014

(65) Prior Publication Data
US 2015/0290020 A1 Oct. 15, 2015

Related U.S. Application Data

(60) Provisional application No. 61/995,548, filed on Apr. 14, 2014.

(51) Int. Cl.
A63B 23/025 (2006.01)
A61F 5/042 (2006.01)

(52) U.S. Cl.
CPC .................... A61F 5/042 (2013.01)

(58) Field of Classification Search
CPC ............ A63B 2023/006; A63B 21/0023
See application file for complete search history.

(56) References Cited

U.S. PATENT DOCUMENTS 3,921,222 A * 11/1975 Hollman ................ A63B 71/12
2/463
4,335,875 A * 6/1982 Elkin .................. A63B 69/0059
482/131
4,337,938 A * 7/1982 Rodriguez ......... A63B 69/0059
224/258
5,069,449 A * 12/1991 Wardwell ............ A63B 21/151
482/126
5,207,627 A * 5/1993 Doran ................... A61H 1/0218
482/114
5,450,995 A * 9/1995 Perrin ..................... A45C 13/30
224/254
5,514,059 A * 5/1996 Romney ............. A63B 21/0004
482/121

(Continued)

OTHER PUBLICATIONS

Magnetic Posture Corrector, Whatever Works, ©2015, http://www.whateverworks.com/itemdy00.aspx?T1=KB4292+L, accessed on Jan. 1, 2015, 1 page.

(Continued)

Primary Examiner — Loan H Thanh
Assistant Examiner — Rae Fischer
(74) Attorney, Agent, or Firm — Duane Morris LLP

(57) ABSTRACT

A therapeutic stretching device includes a strap; a fulcrum member centrally located on the strap and arranged to be placed behind the back of a user's neck and operable as a fulcrum for cervical spinal extension; first and second shoulder pads attached to the strap on either side of the fulcrum member, the shoulder pads arranged to assist the strap in pulling shoulder joints of the user backwards and to create bilateral glenohumeral external rotation; and at least one pair of loops disposed on the strap, wherein shoulder pads are disposed between the fulcrum member and the pair of loops, the loops being disposed and sized for right and left hand or wrist placement during use.

14 Claims, 9 Drawing Sheets

(56) References Cited

U.S. PATENT DOCUMENTS 8,343,018 B2 * 1/2013 Moulton ............ A63B 21/0004
482/131

OTHER PUBLICATIONS

ER Xforce Posture Brach Shoulder Back Support Belt Pain Relief, http://www.amazon.com/BESTSELLER-Posture-Corrective-Shoulder-Corrector/dp/B00GR9P9FO/ref=sr_1, accessed on Jan. 1, 2015, 6 pages.

Duro-Med—Posture Perfect Unisex Back Support Harness, © 2014 Express Medical Supply, Inc., http://www.exmed.net/p-3417-duro-med-posture-perfect-unisex-back-support-harness.aspx; accessed on Jan. 1, 2015, 3 pages.

Duro-Med Posture Corrector, White, http://www.amazon.com/Duro-Med-Posture-Corrector-White-Medium/dp/B000FGXV50, accessed on Jan. 1, 2015, 4 pages.

Deluxe Clavicle Support for Fractures, Sprains, Shoulder Posture Support, FLA Orthopedics; http://www.amazon.com/Deluxe-Clavicle-Support-Medium-80-95cm/dp/B00BT0YB46/ref=sr_1_2?s=hpc&ie=UTF8&qid=1421778256&sr, accessed on Jan. 1, 2015, 4 pages.

The Pettibon System®, 6-Way Stretch Strap Sheets, http://pettibonsystem.com/product/6-way-stretch-strap-sheets, accessed on Jan. 2, 2015, 2 pages.

The Pettibon System® Lycra Covered Mini Cervical Dorsal (Combo Block) Fulcrum, http://pettibonsystem.com/product/lycra-covered-mini-cervical-dorsal-combo-block-fulcrum, accessed on Jan. 2, 2015, 1 page.

Circular Traction—the CRCollar™, the Wedge™, the CRBrace™, the Pro-Lordotic Neck Exerciser™ and the Pope Two-Way Traction Unit, Circular Traction Supply, http://www.circulartraction.com/products.html, accessed on Jan. 1, 2015, 5 pages.

Neck Solutions, Home Neck Traction Devices, Chiropractor Recommended Neck Traction Devices, http://www.necksolutions.com/neck-traction.html, accessed on Jan. 1, 2015, 3 pages.

OPTP Stretch Out Strap with Exercise Booklet, sold by Healthy Deals, http://www.amazon.com/OPTP-Stretch-Strap-Exercise-Booklet/dp/B00065X222/, accessed on Jan. 2, 2015, 5 pages.

The Body-Aline Exercise Device, © 2014 Curve™ LLC (Body-Aline), http://improveposturenow.com/, accessed on Jan. 1, 2015, 7 pages.

Posture Corrector, Core Products International, Inc., http://www.coreproducts.com/posture-corrector.html, accessed on Jan. 1, 2015, 2 pages.

TheraBand™ Stretch Strap, © 2014 The Hygenic Corporation, http://www.thera-band.com/store/products.php?ProductiD=74, accessed on Jan. 4, 2015, 4 pages.

Optec CTO Neck/Back Brace, The Brace Shop, http://www.braceshop.com/optec-cto-cervical-thoracic-orthosis.htm, accessed on Jan. 4, 2015, 2 pages.

Cervical Seated 2-Way Compression Traction, Chiropractic BioPhysics, © 2015 Chiropractic BioPhysics, http://chiropractic-biophysics.myshopify.com/products/cervical-seated-2-way-compression-traction, accessed on Jan. 4, 2015, 2 pages.

Harness for Core Cervical Traction System, © 2015 ScripHessco, http://www.scriphessco.com/products/harness-for-core-cervical-traction-system, accessed on Jan. 4, 2015, 2 pages.

Real-Ease Neck and Shoulder Relaxer, by Real-Ease, http://www.amazon.com/Real-Ease-Neck-and-Shoulder-Relaxer/dp/B000BMI4SW/, accessed on Jan. 4, 2015, 6 pages.

Body-Solid Shoulder Horn Harness, http://www.leisurefitness.com/Body-Solid-Shoulder-Horn-Harness-Medium-P637.aspx, accessed on Jan. 4, 2015, 1 page.

The Neck Curve Restorer Cervical Spine Rehab Device by Hill Therapeutics & Dr. Hargis DC, DABCO, Hill Laboratories Company, http://www.hilllabs.com/therapeutics/Curve-Restorer-Spine-Rehab.php, accessed on Jan. 1, 2015, 2 pages.

Underworks Posture Perfect Band, by Underworks, http://www.amazon.com/Underworks-409-Posture-Perfect-Band/dp/B0002TUH8O/, accessed on Jan. 1, 2015, 6 pages.

PostureNOW Posture Brace, http://www.backbonerestored.info/trusted%20posture%20pages/posture%205.htm, accessed on Jan. 1, 2015, 5 pages.

Cervical Traction Unit®, http://www.backbonerestored.info/trusted%20posture%20pages/posture%205.htm, accessed on Jan. 1, 2015, 2 pages.

Posture Pump® Dual Disc Hydrator, http://www.posturepump.com/, accessed on Jan. 4, 2015, 5 pages.

Products from ScripHessco 2015 Catalog, Cover Page, p. 87 (pillows & cushions), p. 109 (orthopedics) and p. 147 (exercise & rehab), 4 pages.

Products from CHIROONESOURCE 2014 Chiropractic Supply Catalog, Cover Page and p. 65 (orthopedics), 2 pages.

* cited by examiner

CORRECTIVE CERVICAL STRETCHING DEVICE

CROSS REFERENCE TO RELATED APPLICATIONS

This application claims the benefit of and priority to prior filed provisional patent application No. 61/995,548 filed Apr. 14, 2014, the entirety of which is hereby incorporated by reference herein.

FIELD OF THE INVENTION

The present disclosure relates generally to orthopedic correction devices and apparatus, and more specifically relates to devices for providing relief, therapeutic stretching, and correction of forward head position, loss of the normal cervical lordotic curve (i.e., excessive sagging of the spine), and excessive internal shoulder rotation.

BACKGROUND OF THE INVENTION

Forward head positioning and internal shoulder rotation are increasingly observed maladies in our society. As is well known to orthopedists, chiropractors, physical therapists, and other health care practitioners, the human head in its normal position should sit in a direct fashion on the neck and shoulders, with the shoulders in a neutral position. In part, because of various increasing habits in our society, the head can gradually become displaced from a normal, healthy posture of sitting directly on the neck and shoulders, to that of being displaced forward of that normal position. The phrase "forward head posture" (or "FHP") has been used to describe this situation. FHP, combined with its often accompanying excessive internal shoulder rotation (or EISR), has indeed become so widespread, that it may already constitute a health hazard having ramifications that are pediatric, geriatric, orthopedic, and possibly systemic in nature, since when left untreated, FHP/EISR can develop degenerative and disabling joint diseases affecting countless numbers of people.

There are many reasons why FHP/EISR is developing into a more pervasive problem. The increasing use of computer screens can cause the user to move and maintain the head and shoulders in FHP/EISR. Handheld devices such as smart phones and touch pads have become common place, causing the user to maintain prolonged head flexion and internal shoulder rotation. The problem is seen in children and young adults who, in many cases, spend extended periods of time with texting, video games, and watching television.

The damage resulting from FHP/EISR is tied to the cervical portion of the spine becoming chronically fixated and misaligned into flexion. Additionally, prolonged internal rotation of the shoulder joints can contribute to skeletal distortion and function. Collective distortion of posture in this manner can lead to excessive tightening and eventual shortening of many important muscles, such as the levator scapula, upper trapezius, sternocleidomastoid, pectoralis (major and minor), anterior deltoid, and latissimus dorsi, to name a few. When the origin and insertion of a muscle excessively proximate for prolonged periods of time, the fibers begin to permanently shorten. "Davis' law" describes soft tissues' tendency to shorten and contract unless subject to frequent stretching. Other muscles, on the other hand, tend to become under active and weaken, such as the rhomboids (major and minor), mid trapezius, and posterior deltoids. The result of this imbalance, also in part due to the occulo-pelvic reflex (NASM), causes the entire body to adjust its normal, healthy posture in order to adapt to the distortion.

Health issues arising from FHP/EISR are well known and recognized in the health field as being potentially serious in nature, as described above. Although efforts to correct these issues by treatment with orthopedic devices available on the market have enjoyed varying degrees of success, many of these devices require going to a physician's office or facility, finding the time and place for lying down supine on the device, or wearing an inconvenient and cumbersome apparatus. Further, most of these devices are designed to effect change to FHP (and in some cases, address the cervical lordotic curve), but fail to effectively address the accompanying EISR that often accompanies FHP.

Most cervical collars are designed to immobilize the neck and/or cause axial translation to decompress the cervical spine while causing cervical spine straightening. Use of cervical collars may produce mixed benefits. Ligament impairment cannot improve around a straightened cervical curve (due to this abnormal alignment), which will ultimately result in permanent arthritic changes to the cervical joints. Ligament and muscle/tendon rehabilitation requires improvement of joint alignment, as well as lengthening of the related shortened and over active muscles, over time. As with any corrective orthopedic device, an accompanying exercise program designed to strengthen concomitant weakened muscles is also desired and recommended.

Devices are available for providing assistance in correcting reduced or reversed cervical curvature, forward head position, and excessive internal shoulder rotation. These devices are designed to assist in cervical remodeling, correctively exercising, stretching, and repositioning the cervical spine and upper torso.

SUMMARY OF THE INVENTION

A therapeutic stretching device includes a strap; a fulcrum member centrally located on the strap and arranged to be placed behind the back of a user's neck and operable as a fulcrum for cervical spinal extension; first and second shoulder pads attached to the strap on either side of the fulcrum member, the shoulder pads arranged to assist the strap in pulling shoulder joints of the user backwards and to create bilateral glenohumeral external rotation; and at least one pair of loops disposed on the strap, wherein shoulder pads are disposed between the fulcrum member and the pair of loops, the loops disposed and sized for right and left hand or wrist placement during use.

The above and other features of the present invention will be better understood from the following detailed description of the preferred embodiments of the invention that is provided in connection with the accompanying drawings.

BRIEF DESCRIPTION OF THE DRAWINGS

The accompanying drawings illustrate preferred embodiments of the invention, as well as other information pertinent to the disclosure, in which.

DETAILED DESCRIPTION

Figure 1:
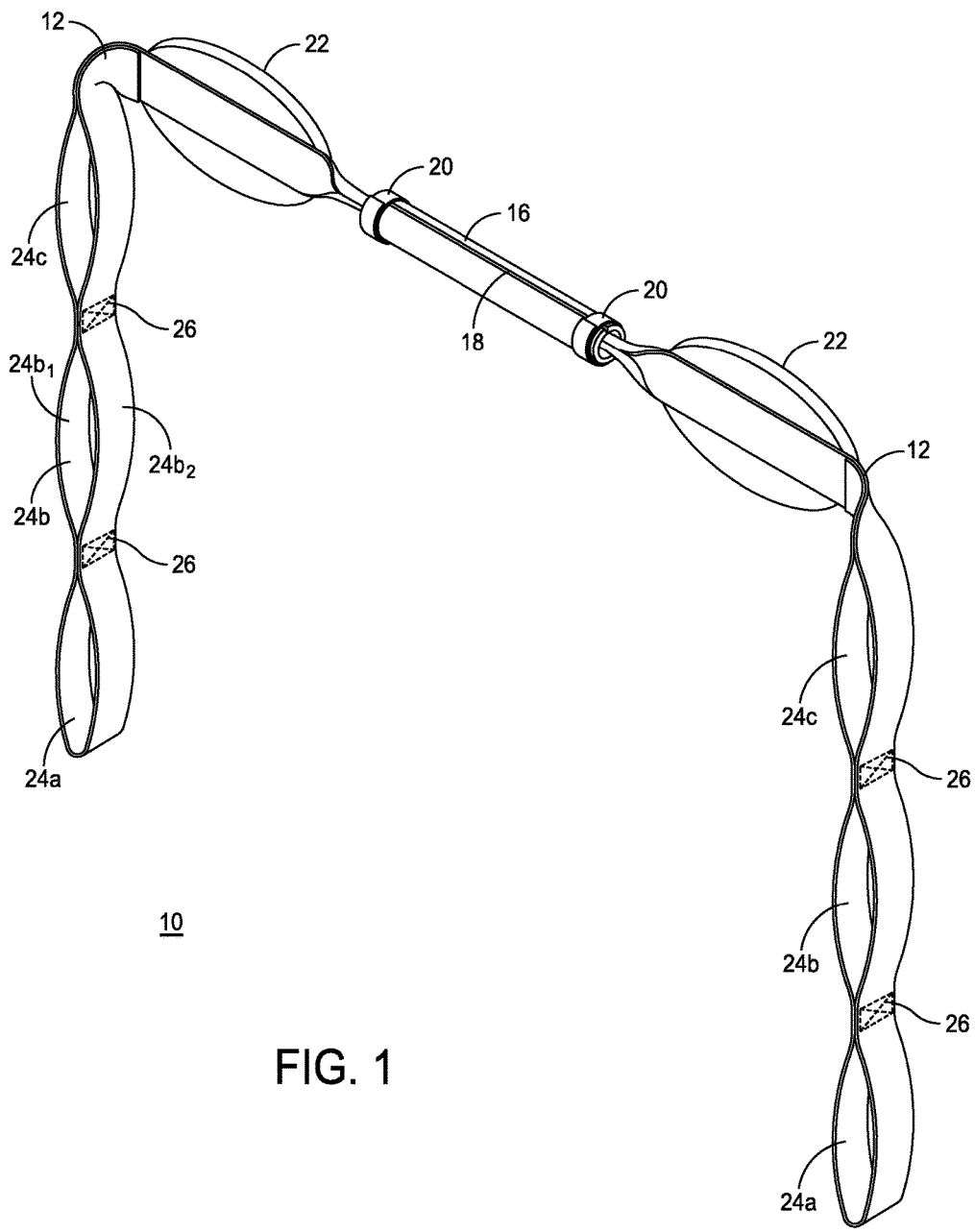
FIG. 1 is a perspective view of an embodiment of a corrective stretching device.
Figure 2:
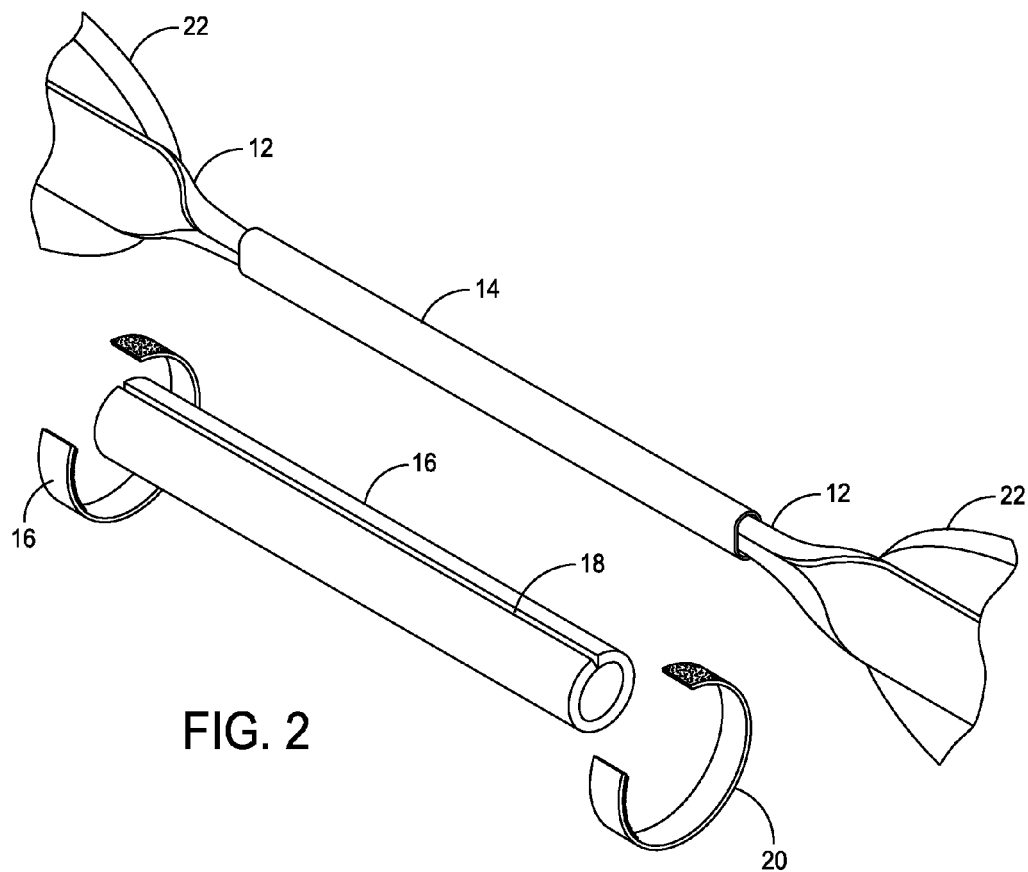
FIGS. 2 and 3 are partial perspective views of the corrective stretching device of FIG. 1.
Figure 3:
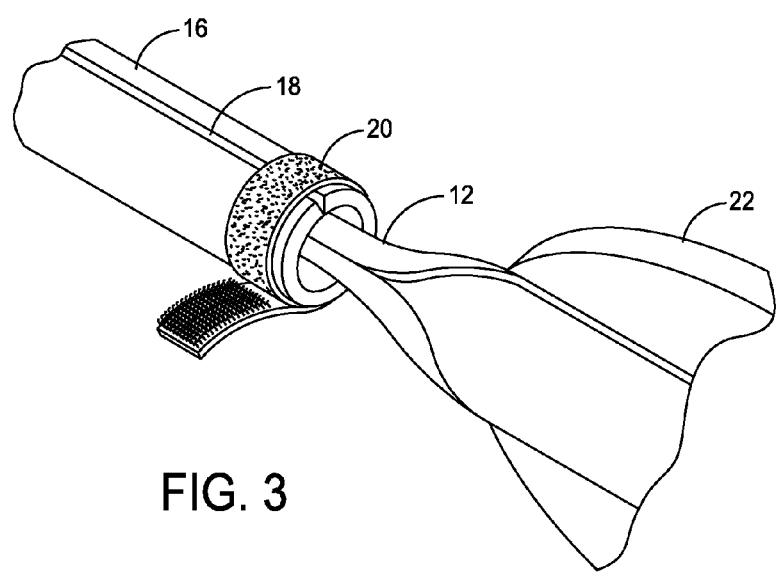
Figure 4:
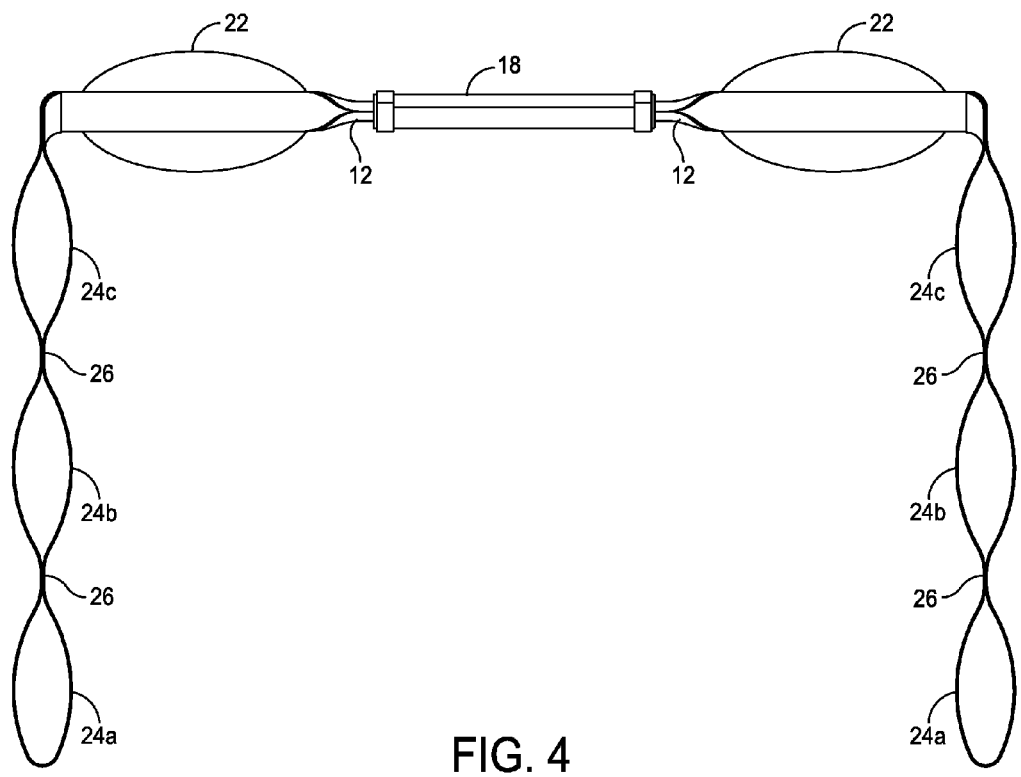
FIG. 4 is a plan view of the corrective stretching device of FIG. 1.
Figure 5:
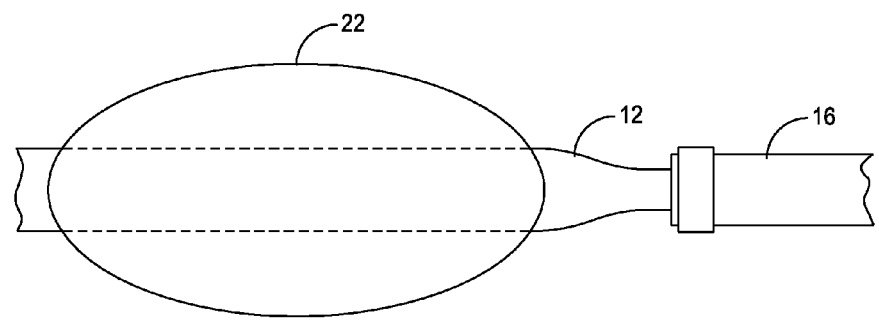
FIG. 5 is a partial plan view of the corrective stretching device of FIG. 1.

This description of the exemplary embodiments is intended to be read in connection with the accompanying drawings, which are to be considered part of the entire written description. In the description, relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

There is a great need for a truly portable, effective, and easy to use method of regularly correctively repositioning and stretching the cervical spine and glenohumeral joints with the least amount of inconvenience possible. There is a concomitant need for a corrective device for use in such a method. By creating convenience and ease of use, an individual is much more likely to utilize the corrective device, therefore enjoying the positive health benefits it provides.

To that end, disclosed herein is a new type of therapeutic corrective device which addresses forward head position (FHP) and/or excessive internal shoulder rotation (EISR). This device utilizes the body's own arm weight to provide the corrective force required to encourage a normal cervical lordotic curve, proper head position, and external shoulder rotation. The orthopedic corrective device can be readily used by a patient suffering from FHP/EISR to reverse the damaging effects of compressive loading, shear, and neck/shoulder movements which FHP/EISR generates at the cervical vertebra and glenohumeral joint, along with the associated involved soft tissue imbalance of the individual.

In embodiments of the device, the device includes a forward head position/internal shoulder rotation correction strap with a cervical fulcrum tube and bilateral shoulder pad assembly, and a strap with hand/wrist loops to assist in proper arm positioning, as well as allowing the arm weight to provide the necessary force to stretch and reposition the neck and shoulders into a corrective position.

In embodiments, the posture correction device is designed to assist in stretching the cervical spine and shoulders into their proper anatomical positions. This device consists of a strap running through a short flexible tube, relative to the length of the strap, which is centered on the entire strap. An additional slitted tube (i.e., tube with a longitudinal slit) covers the inner tube in order to offer the option of less cervical extension for users whose neck cannot initially tolerate full extension. As cervical flexibility increases with adaptation to the device, the outer tube may be easily removed to provide increased cervical extension. There are two pads adjacent to this tube, with one on either side of the tubing. This is followed by three loops sewn consecutively into the strap on both sides. The central rubber tube is placed behind the neck and the strap hangs down freely on either side anteriorly. The right and left hands slide through the loops, respectively, up to the wrists. The three consecutive loops on either side are designed to accommodate individuals of different heights and arm lengths. The pads are aligned with the anterior portion of both shoulders, covering the glenohumeral joints. The individual then positions both hands behind their back, keeping the wrists in the loops. The head is then extended back to its maximum position, as comfort will allow.

The weight of the arms hanging down cause a posterior to anterior force to be exerted on the cervical rubber tube and an anterior to posterior force to be exerted on the shoulder pads. This pressure creates a fulcrum for the neck, encouraging proper cervical lordosis as well as corrective external rotation of the glenohumeral joint simultaneously.

Now, with reference to the figures, specifically, FIGS. 1-6, a stretching device, particularly a therapeutic forward head position/excessive internal shoulder rotation correction device 10 is illustrated. Referring to FIG. 1, in embodiments, the device 10 includes an elongated strap 12 of substantially longer length than width and of nominal relative thickness. In embodiments, the strap has an end-to-end length between about 50 and 100 inches, and more preferably around 50-70 inches in length, a width between about 0.5 to 3 inches, and a thickness between about 0.03 to 1.5 mm. The strap 12 can be comprised of nylon, polypropylene, cotton, or any other functionally supportive material.

In embodiments, the device 10 includes a centrally located fulcrum member, which in the illustrated embodiment is a hollow flexible tube 14 (FIG. 2) through which the strap 12 is pulled. Alternatively, the tube can have a longitudinal opening or slit (not shown) formed therein that allows the tube to be centered lengthwise on the strap. In such an embodiment, the tube can be secured in place with one or more hook and loop fasteners (e.g., Velcro® fasteners), buttons, adhesive, tape or any other means of securely closing the tube 14 around the strap 12 as needed. In embodiments the hollow flexible tube 14 has a length of between about 5-9 inches and an outer diameter between about 0.8 to 3 inches. In one embodiment, the tube 14 has an internal diameter of 0.550 inches and wall thickness of 0.300 inches. In embodiments, the tube 14 has a density (b./cu ft.) of about of 11-15 lbs.

In embodiments, a second, wider hollow flexible tube 16 of approximate equal length is placed around the tube 14. In the illustrated embodiment, the tube 16 has a longitudinal slit 18 formed therein to facilitate opening the tube to fit it around the tube 14. One or more Velcro® fasteners 20 can be provided at either end of the tube 16 that wrap around the tube 16 to secure it in the closed arrangement around the tube 14. Of course, the fasteners can be built into the tube 16. Further, tubes 16 can be provided in different sizes and diameters as needed as part of a therapeutic system. Of course, additional tubes can also be used (e.g., a third slitted tube can be provided as part of the system). The thickness of the tubes separates the strap 12 from the user's neck and adjusts the amount cervical extension permitted by the device 10. The tubes 14, 16 may be constructed of any flexible resilient material, such as rubber, polyurethane foam, or any other functional material.

The device 10 preferably includes two (left and right) shoulder pads 22 attached to (e.g., adhered, sewn, buttoned, snapped or otherwise fixed to) the strap 10 on either side of central fulcrum member, e.g., tubing 14, 16. In embodiments, the pads 22 can be attached to the strap in an adjustable manner that allows the position of the pads 22 to adjusted along the strap 12. For example, the pads can be connected to the strap at different positions with mating fasteners, or the strap 12 can extend through a back loop or loops of the strap so that the strap can be slid into position along the strap 12. Embodiments of an adjustable shoulder pad are described in more detail in connection with FIGS. 11-11C. In embodiments, each the shoulder pad 22 is approximately 1 to 12, and in embodiments 5 to 8, inches in length, and in embodiments 1 to 6, inches in width, and 0.25 to 3 inches in thickness. In embodiments, the shoulder pads 22 have an oval shape but may also be oval, square, rectangular, circular, triangular, cupped and/or irregular in shape. Each pad 22 can be located from about 0 inches to 4 inches distally from the closest end of the tubing 14, 16. The shoulder pads may be made from polyurethane foam, nitrile foam, neoprene, gel, foam rubber, or any other material that provides a durable, padded body.

Figure 10:
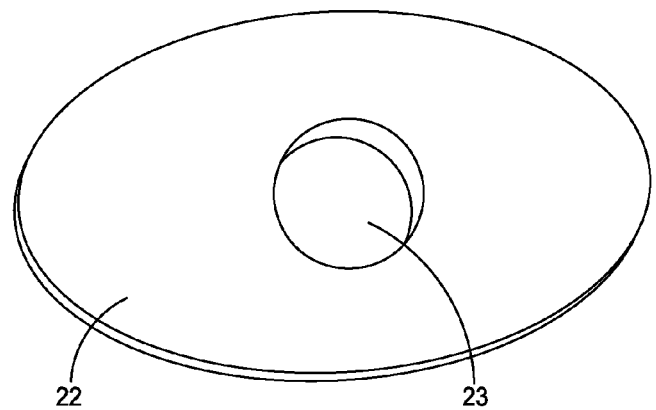
FIG. 10 illustrates an embodiment of a shoulder pad of a corrective stretching device.

In embodiments (see FIG. 10), the shoulder pad 22 may have a central cutout or hole (for example 1.5 inches in diameter) to improve stabilization on the shoulder. The shape of the shoulder pad cutout can be circular, oval, square, triangular or any other functional shape.

In embodiments, the strap 12 can have an original length between about 60 to 200 inches, and more preferably between about 100-105 inches. The strap 12 is folded over on itself at each end for approximately 16-38 inches, and in embodiments for about 19 inches, creating a loop at each end. From this loop, two or more smaller loops 24 are formed by, for example, pinching the strap 12 to itself. In the illustrated embodiment, the device has 6 total loops 24, 3 on each side, providing three loop pairs 24a, 24b, 24c. The strap 12 can be connected to itself to form loops in any suitable manner, such as using an adhesive, crimping, staples or other fasteners, heat bonding, or sewing. In embodiments, the strap 12 is sewn to itself at connection points or regions 26 with 0.5 to 1.5 inch stitch area between each loop, which provides proper support of the arms as discussed below. Of course, rather than looping the strap 12 back on itself to create loops 24, smaller, separate strips of strap each having a length between about 4 to 6 inches can be connected to the strap 12 to create loops 24.

The loops 24 are positioned and sized for hand and wrist placement, with each of the three left/right pairs of loops 24a, 24b, 24c intended to accommodate persons of differing heights and arm lengths. For each loop internal loop 24b, 24c, the overlying portion of the strap preferably provides for approximately one more inch of strap length than the underlying portion of the strap. For example, the length of the overlapping portion $24b_2$ of the strap 12 can be greater than the length of the overlapped portion $24b_1$ of loop 24b. This creates excess strap material on one side of the loop, allowing for ease of entry for the hands and wrists.

The stretching device 10 is designed to allow for simultaneously creating a fulcrum for cervical lordotic correction, excessive internal shoulder rotation correction, and forward head position correction, using body positioning with the device 10 and arm weight as the means to exert corrective force on the aforementioned anatomical areas. The device 10 can be used to treat the postural condition now known as Cervical Kyphosis/Forward Head Posture Syndrome/Excessive Internal Shoulder Rotation. In order to correct this potentially crippling condition, the patient's neck curve must be supported at the cervical vertebrae that are causing the reversal of the neck curve while simultaneously repositioning the head rearward to align over the shoulders and rotating the shoulders in a posterior-lateral line of correction. The device 10 is designed to assist in this alignment. More specifically, the device 10 is designed to assist in stretching the cervical spine and shoulders into their proper anatomical positions. Use of the additional (one or more) slitted tube 14 offers the option of less cervical extension for users whose neck cannot initially tolerate full extension. As cervical flexibility increases with adaptation to the device, the outer tube may be easily removed to provide increased cervical extension.

Figure 6:
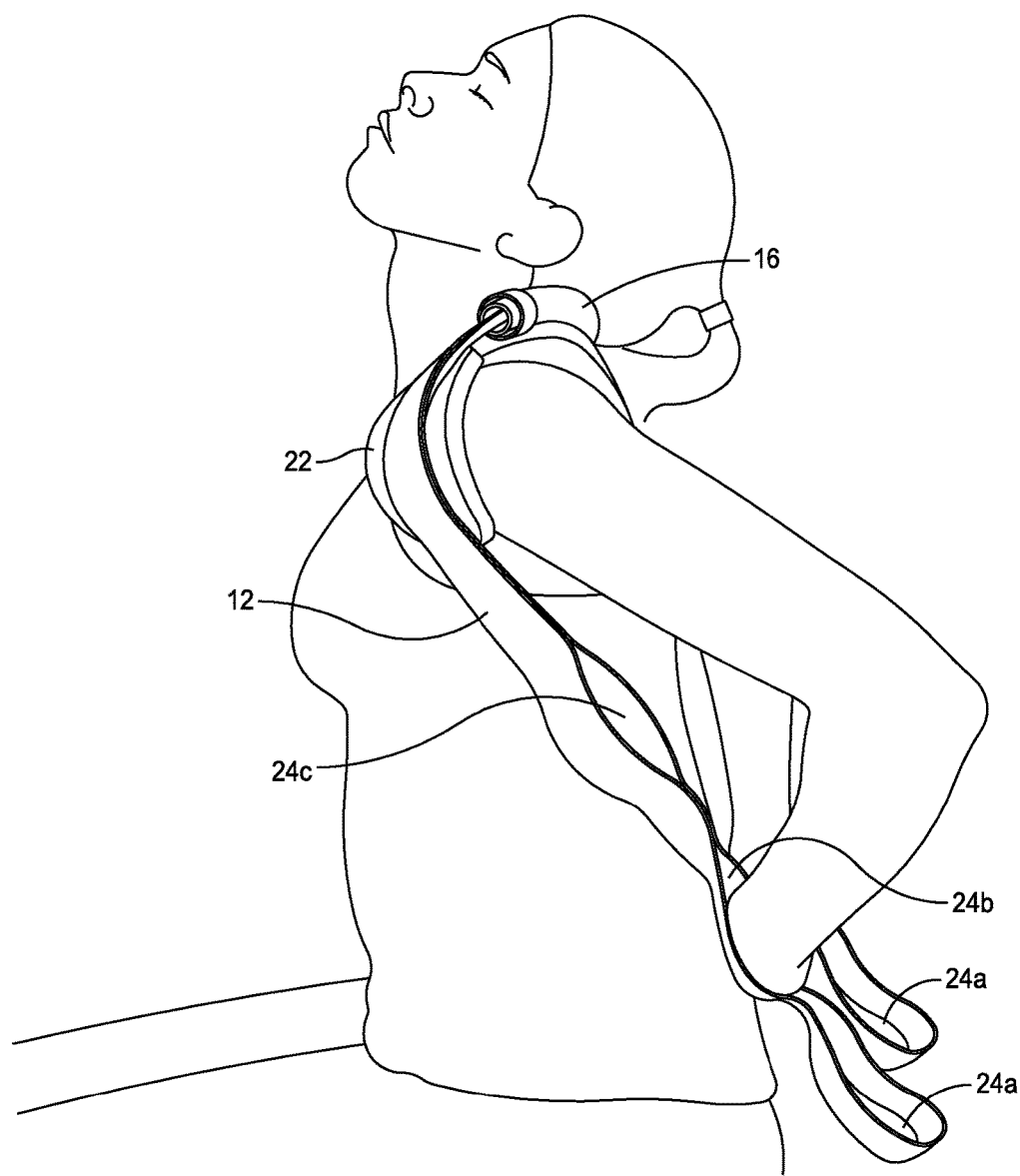
FIG. 6 illustrates the corrective stretching device of FIG. 1 in use.

In use, as illustrated in FIG. 6, the central rubber tube 14 (with or without additional tube 16 disposed around the tube 14) is placed behind the neck with the strap 12 hanging down freely on either side anteriorly. The user slides the right and left hands through a pair of the loops 24a, 24b or 24c, respectively, up to the wrists. Again, the pairs of consecutive loops 24 are designed to accommodate individuals of different heights or arm lengths. The shoulder pads 22 are positioned along the anterior portion of both shoulders, covering the glenohumeral joints. The individual then positions both hands behind their back, keeping the wrists in the loops. The head is then extended back to its maximum position, as comfort will allow.

Per the foregoing, a method of therapeutic stretching using the stretching device described herein includes: locating the fulcrum member behind a neck of a user; positioning the shoulder pads along the anterior portion of both shoulders of the user, covering the glenohumeral joints; disposing right and left hands through the pair of the loops; positioning both hands behind the user's back, with wrists of the user in the loops; and extending the user's head back towards its maximum position.

The weight of the arms hanging down cause a posterior to anterior force to be exerted on the cervical rubber tube(s) 14, 16 and an anterior to posterior force to be exerted on the shoulder pads. These forces create a fulcrum for the neck, encouraging proper cervical lordosis as well as corrective external rotation of the glenohumeral joint simultaneously.

Figure 7A:
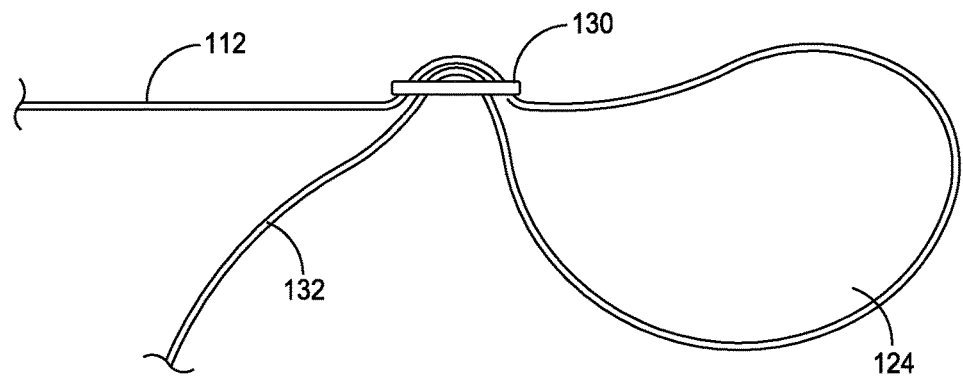
FIGS. 7A and 7B illustrate an alternative embodiment of a corrective stretching device having an adjustable loop portion.
Figure 7B:
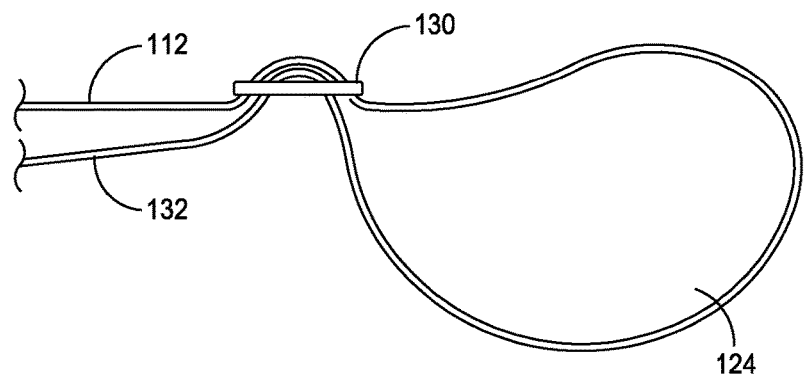

It should be understood that while the device 10 is illustrated as having three loops 24 on either side of the device, forming three pairs of loops 24a, 24b, 24c, other configurations are also contemplated. For example, the device 10 can have only one pair of loops and come in different lengths to accommodate patients of different sizes. The device 10 could also have two pairs of loops 24, four pairs of loops 24 or other number of loops as needed. Further, the device could have a single pair of loops, with one loop on either side of the device, but with the location of the loops relative to the center of the device 10 being adjustable. This adjustability can be provided in any number of ways. One such embodiment is illustrated in FIGS. 7A and 7B. In this embodiment, a slider 130 (also known as a slide adjuster or tri-glide) is provided. The relative location of each loop 124 can be adjusted by adjusting the position of the slider 130 along the length of strap 112 and the amount of strap 112 pulled through the slider 130 from the free ends 132.

Figure 8A:
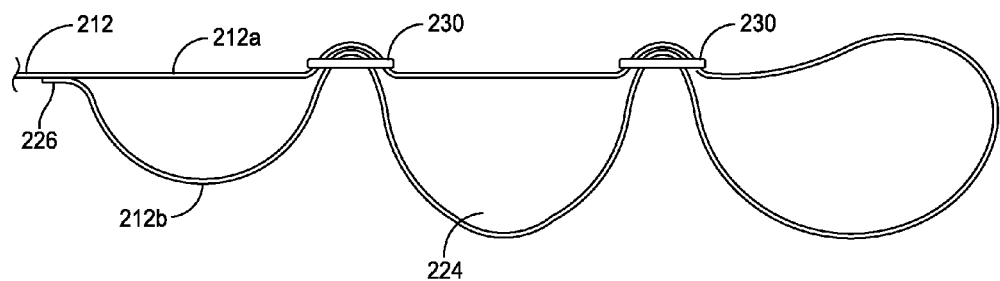
FIGS. 8A and 8B illustrate another embodiment of a corrective stretching device having an adjustable loop portion.
Figure 8B:
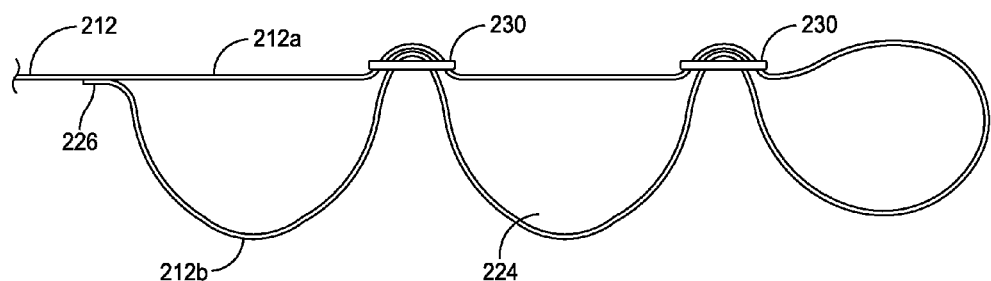

In an alternative embodiment shown in FIGS. 8A and 8B, portions 212a, 212b of the strap 212 can be overlapped and secured at a connection point 226 proximate the shoulder pads (not shown) to form a large loop. While only one end of the device is illustrated, it should be apparent that a similar configuration is provided on each side of the device. In this embodiment, two sliders 230 are provided along the length of the larger loop to form a smaller loop 224 sized for hand or wrist placement of the user. As can be seen in FIGS. 8A and 8B, the position (and size) of this smaller loop 224 can be adjusted by moving the sliders 230 and adjusting the amount of slack on either side of the loop 224.

Figure 9A:
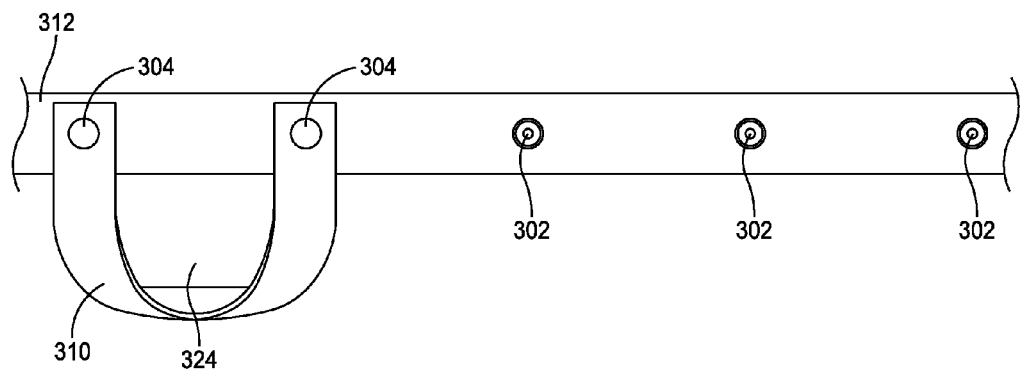
FIGS. 9A and 9B illustrate another embodiment of a corrective stretching device having an adjustable loop portion.
Figure 9B:
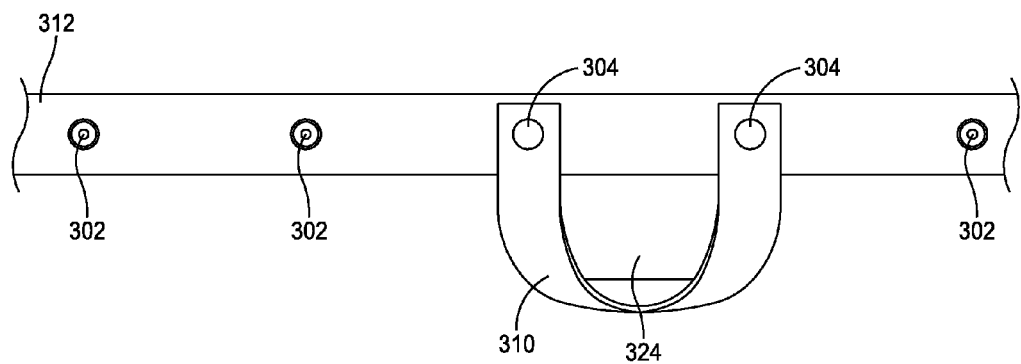

In yet another embodiment illustrated in FIGS. 9A and 9B, the strap 312 can be provided with a number of spaced male snap on button halves 302. A separate piece of strap 310 that is sized properly to form a loop 324 with the strap 312 is provided with two spaced female snap on button halves 304. As can be seen in FIGS. 9A to 9B, the location of the loop 324 can be changed simply by buttoning the strap piece 310 to different combinations of adjacent male button halves 302 of the strap 312. It should be understood that while snap on buttons are illustrated in the figures, other forms of buttons, such as a Jeans button and tack arrangement or other button or fastener arrangements (e.g., Velcro®, adhesive, buckle or other fastener) can be used.

Figure 11:
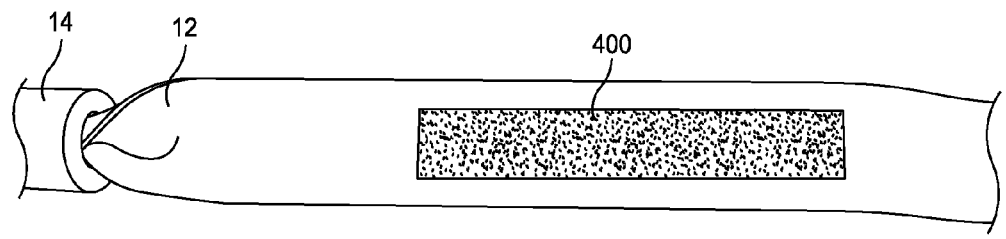
FIGS. 11-11C illustrate an embodiment of a corrective stretching device having a shoulder pad whose location can be adjusted.
Figure 11A:
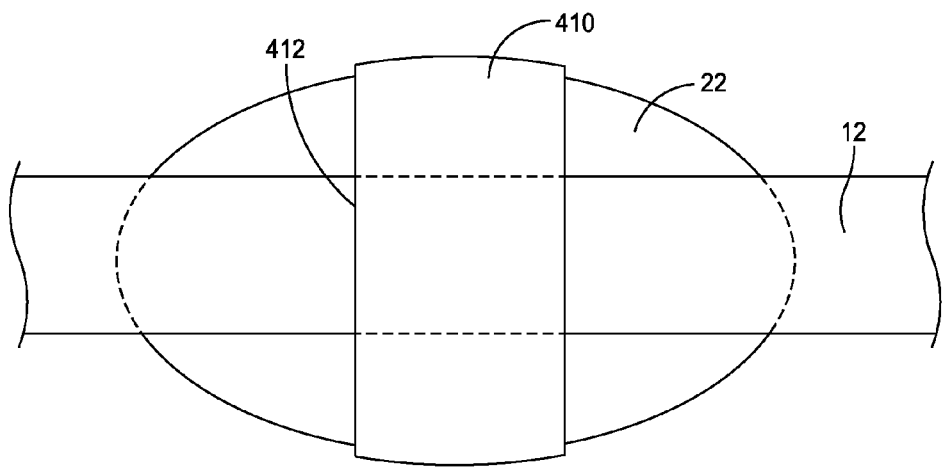
Figure 11B:
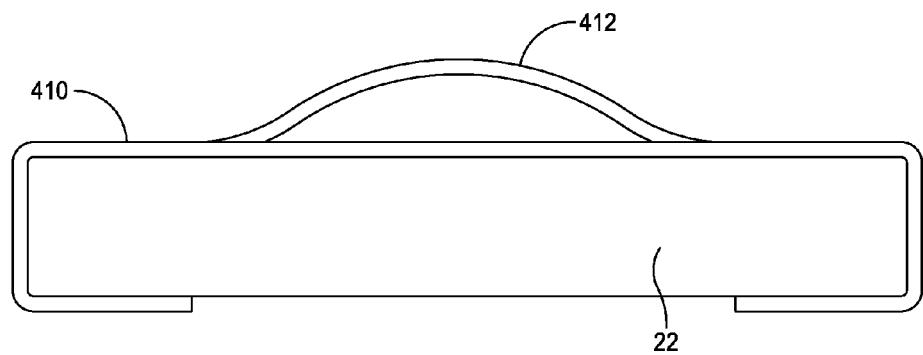
Figure 11C:
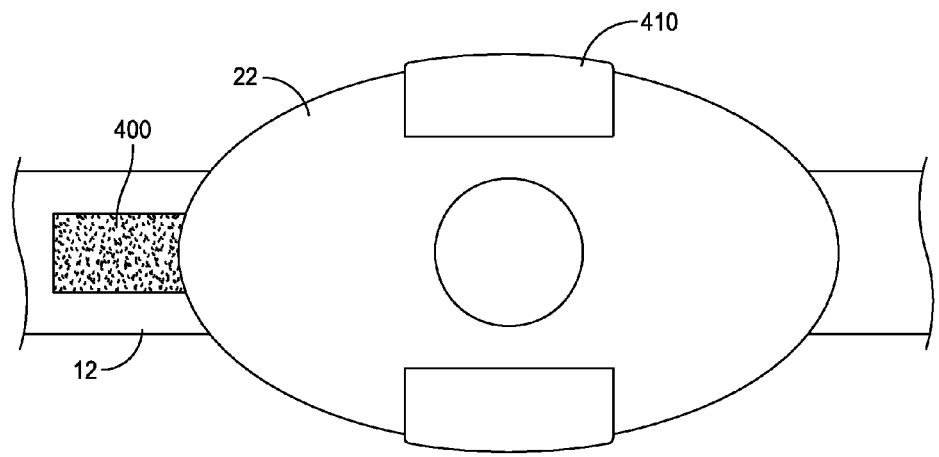

FIGS. 11A-11C illustrate an embodiment of a corrective stretching device having an adjustable location shoulder pad. FIG. 11 illustrates a partial view of the corrective stretching device discussed above. In the illustrated embodiment, the strap includes a short strip of material (such as a ¾ to 1 inch wide by 5-6 inch long strip of hook and loop material) for providing friction or drag that assists a slidable shoulder pad to stay in place once set in the desired position. FIG. 11A is a partial rear view of the corrective stretching device showing the shoulder pad connected to the strap 12 in a slidable fashion. Specifically, a short strap 410 (e.g., a 6 inch long by 2 inch wide polypropylene strap (0.04 mm in thickness)) is connected (e.g., stitched) to the shoulder pad 22. The short strap 410 includes a shorter loop section 412 (shown in the close up view of FIG. 11B) that forms a channel through which the strap 12 extends. As shown in FIG. 11C, the position of shoulder pad 22 can be adjusted along the length of the strap 22, with the frictional material 400 on the strap 12 engaging the material of the short loop section 412 to help secure the shoulder pad in place (i.e., by providing resistance against sliding).

Of course, in an alternative embodiment, the rear surface of shoulder pad 22 can be provided with a strip of material (e.g., and hook and loop fastener strip) for mating with a corresponding strip on strap 12 (e.g., strip 400 of hook and loop fastener material), and the shoulder pad can located in the desired location along the strap 12 and then secured in place. In this embodiment, the device may or may not be provided with a strap section that wraps around the strap 12. Of course other means of fastening the shoulder pads to different locations along the strap 12 may also be employed, for example, buttons, clips, adhesives, or other mechanical fasteners.

Although the invention has been described in terms of exemplary embodiments, it is not limited thereto. Rather, the appended claims should be construed broadly to include other variants and embodiments of the invention that may be made by those skilled in the art without departing from the scope and range of equivalents of the invention.

What is claimed is:

1. A therapeutic stretching device comprising:
   a continuous length of strap having a first end, a second end and a middle portion disposed between the first and second ends, the continuous length of strap being of substantially longer length than width;
   a fulcrum member centrally located on the strap at the middle portion of the continuous length of strap and arranged to be placed behind the back of a user's neck and operable as a fulcrum for cervical spinal extension, the fulcrum member comprising a hollow tube member disposed around the middle portion of the continuous length of strap, the tube member having a length between about 5-9 inches and an outer diameter smaller than the width of the strap and greater than the thickness of the strap;
   first and second shoulder pads distinct from the continuous length of strap and attached to the strap on either side of the fulcrum member, the shoulder pads being wider than the straps and shaped to cover left and right glenohumeral joints of the user when positioned along the anterior portion of the user's shoulders, the shoulder pads being configured to assist the strap in pulling shoulder joints of the user backwards and to create bilateral glenohumeral external rotation when the user's arms are located behind the user's back; and
   first and second loops fixedly disposed on the strap proximate the first and second ends of the continuous length of strap, respectively, wherein shoulder pads are disposed between the fulcrum member and the loops, the loops being disposed and sized for right and left hand or wrist placement during use,
   wherein the stretching device comprises third and fourth loops fixedly disposed at a different distance from the centrally located fulcrum member than the first and second loops to accommodate users of different heights or arm lengths, the first, second, third and fourth loops being equally sized.

2. The therapeutic stretching device of claim 1, further comprising a second fulcrum member, the second fulcrum member configured to be removably fitted around the centrally located fulcrum member, thereby increasing the thickness of the fulcrum member.

3. The therapeutic stretching device of claim 2, wherein the second fulcrum member comprises a hollow tube member with a longitudinal slit.

4. The therapeutic stretching device of claim 1, wherein each loop is formed from a respective portion of the strap that is overlapped with another portion of the strap and fixed to the strap.

5. The therapeutic stretching device of claim 1, wherein the device has a length between about 50-70 inches, a width between about 0.5 to 3 inches, and a thickness between about 0.03 to 1.5 mm.

6. The therapeutic stretching device of claim 1, wherein the centrally located fulcrum member is formed from a resilient material.

7. The therapeutic stretching device of claim 6, wherein the centrally located fulcrum member is formed from rubber or foam material.

8. The therapeutic stretching device of claim 1, wherein the shoulder pads are configured for removal from the strap for repositioning to different positions along the length of the strap.

9. A therapeutic stretching device, comprising:
   a continuous length of strap having a first end, a second end and a middle portion disposed between the first and second ends, the continuous length of strap being of substantially longer length than width;

a fulcrum member centrally located on the strap at the middle portion of the continuous length of strap and arranged to be placed behind the back of a user's neck and operable as a fulcrum for cervical spinal extension, the fulcrum member comprising a hollow tube member disposed around the middle portion of the continuous length of strap, the tube member having a length between about 5-9 inches and an outer diameter smaller than the width of the strap and greater than the thickness of the strap;

first and second shoulder pads distinct from the continuous length of strap and attached to the strap on either side of the fulcrum member, the shoulder pads being wider than the straps and shaped to cover left and right glenohumeral joints of the user when positioned along the anterior portion of the user's shoulder, the shoulder pads being configured to assist the strap in pulling shoulder joints of the user backwards and to create bilateral glenohumeral external rotation when the user's arms are located behind the user's back;

a plurality of pairs of equally sized loops fixedly disposed on the strap, wherein shoulder pads are disposed between the fulcrum member and the pairs of loops, respective pairs of loops disposed at different distances from the fulcrum member to accommodate users of different heights or arm lengths and sized for right and left hand or wrist placement during use; and a second fulcrum member, the second fulcrum member comprising a second hollow tube member having approximately equal length as the first fulcrum member, having an outer diameter greater than the diameter of the fulcrum member, sized to fit around the fulcrum member and configured for removable attachment around the fulcrum member, wherein the second fulcrum member can be removed to provide for increased cervical extension as cervical flexibility of the user increases with adaptation to the device.

10. The therapeutic stretching device of claim 9, wherein the second hollow tube member has a longitudinal slit for allowing the second hollow tube member to be disposed around the first hollow tube member.

11. The therapeutic stretching device of claim 9, wherein each loop of the pairs of the loops is formed from a respective portion of the strap that is overlapped with another portion of the strap and fixed to the strap.

12. A therapeutic stretching device comprising:

a strap, the strap being of substantially longer length than width;

a fulcrum member centrally located on the strap and arranged to be placed behind the back of a user's neck and operable as a fulcrum for cervical spinal extension, the fulcrum member comprising a hollow tube member disposed around a middle portion of the strap, the tube member having a length between about 5-9 inches and an outer diameter smaller than the width of the strap and greater than the thickness of the strap;

first and second shoulder pads attached to the strap on either side of the fulcrum member, wherein the shoulder pads are wider than the strap and shaped to cover left and right glenohumeral joints of the user when positioned along the anterior portion of the user's shoulders, the shoulder pads being configured to assist the strap in pulling the glenohumeral joints backwards and to create bilateral glenohumeral external rotation; and at least one pair of loops fixedly disposed on the strap, wherein shoulder pads are disposed between the fulcrum member and the pair of loops, the loops being disposed and sized for right and left hand or wrist placement during use.

13. The therapeutic stretching device of claim 12, wherein the shoulder pads comprise foam pads.

14. The therapeutic stretching device of claim 12, wherein the shoulder pads are circular, ovular or cup shaped.

* * * * *